US00PP32307P2

(12) United States Plant Patent
Tsunoda

(10) Patent No.: US PP32,307 P2
(45) Date of Patent: Oct. 13, 2020

(54) ***CORNUS FLORIDA L.* PLANT NAMED 'SFCG1702'**

(50) Latin Name: ***Cornus florida* L.**
Varietal Denomination: SFCG1702

(71) Applicants: TSUNODAEN CO., LTD., Inazawa-shi (JP); SUMITOMO FORESTRY LANDSCAPING CO., LTD., Tokyo (JP)

(72) Inventor: Tadayasu Tsunoda, Aichi (JP)

(73) Assignees: TSUNODAEN CO., LTD., Inazawa-shi (JP); SUMITOMO FORESTRY LANDSCAPING CO., LTD., Tokyo (JP)

( * ) Notice: Subject to any disclaimer, the term of this patent is extended or adjusted under 35 U.S.C. 154(b) by 0 days.

(21) Appl. No.: 16/501,290

(22) Filed: Mar. 20, 2019

(51) Int. Cl.
*A01H 5/00* (2018.01)
*A01H 6/00* (2018.01)

(52) U.S. Cl.
USPC ..... Plt./220
CPC ..... *A01H 6/00* (2018.05)

(58) Field of Classification Search
USPC ..... Plt./220
CPC ..... A01H 5/02; A01H 5/00
See application file for complete search history.

(56) References Cited

U.S. PATENT DOCUMENTS

PP11,654 P 11/2000 Asako

OTHER PUBLICATIONS

GTITM UPOVROM Plant Variety Database citation for 'SFCG1702' as per JPPBR32402; Jan. 19, 2018; 1 page.*

* cited by examiner

*Primary Examiner* — Kent L Bell
(74) *Attorney, Agent, or Firm* — Oblon, McClelland, Maier & Neustadt, L.L.P.

(57) ABSTRACT

A new and distinct cultivar of *Cornus florida* L. plant (dogwood tree) named 'SFCG1702', characterized by having upright plant growth habit, extremely large, heart-like shaped and vivid purplish-red pink marginal floral bracts around inflorescence, many flowers on lower branches, elegant rose-like fragrance, and strong disease resistance, especially to powdery mildew.

11 Drawing Sheets

Latin name of the genus and species of the plant claimed: *Cornus florida* L.

Variety denomination: 'SFCG1702'.

BACKGROUND OF THE INVENTION

This invention relates to a new and distinct hybrid cultivar of dogwood tree (*Cornus florida* L.) named 'SFCG1702'. This novel cultivar is the product of cross and selection for a big, pink-bracted dogwood, in this instance the result of an open pollination of white-bracted 'White Love' cultivar (U.S. Plant Pat. No. 11,654), as a seed parent cultivar, with several red-bracted pollen parent cultivars. The cross and selection was carried out for the period from 2006 to 2017 in Heiwa-Town, Inazawa-City, Aichi-prefecture, Japan.

In 2006 spring, the seed parent 'White Love' was open pollinated with pollen from several red-flowering dogwood pollen parent cultivars (all of which were unpatented, and cultivated in Inazawa-City, Aichi-prefecture, Japan). About 5,000 $F_1$ seeds of the cross between 'White Love' and the several red-flowering dogwood pollen parents were collected in 2006 autumn, and these seeds were sprouted in 2007 spring. About 2,500 seedlings from the $F_1$ seeds were transplanted in nursery pots in 2007 winter, and then 400 nursery plants derived from the above about 2,500 seedlings were transplanted in the open-field in 2009 winter.

The first flowering of the $F_1$ trees from the above-identified cross were observed in 2011 spring, and at the time, white flowering trees, pale-yellow flowering trees, and pink flowering trees were found. These trees were flowered again in 2012 spring, and among these, the pink flowering trees were selected as candidate mother trees. In 2013 spring, one pink flowering tree was established as a mother tree of the present 'SFCG1702' cultivar. The shoots from the mother tree were grafted onto seedling rootstocks (all of which were sprouted from the seedlings resulting from the cross between 'White Love' (seed parent) and 'Junior Miss' (pollen parent)), and the investigation of these trees on the plant characteristics of 'SFCG1702' cultivar was commenced in 2015 autumn. This investigation was completed in 2017 spring.

As will be understood from the detailed description of the invention which appears hereinafter, the new cultivar 'SFCG1702' has clearly different characteristics from those of the seed parent cultivar 'White Love', and 'Cherokee Chief' (the representative cultivar of red flowering dogwoods) (U.S. Plant Pat. No. 1,710). 'SFCG1702' is in fact outstanding and readily identified as being such.

The present 'SFCG1702' cultivar has been repeatedly asexually reproduced by grafting onto rootstock in Heiwa-Town, Inazawa-City, Aichi-prefecture, Japan. All trees of 'SFCG1702' have reproduced asexually true to type in successive generations.

SUMMARY OF THE INVENTION

The new dogwood cultivar 'SFCG1702' exhibits outstanding and distinguishing characteristics when grown under normal horticultural conditions, including:

(1) upright plant growth habit;
(2) having extremely large, heart-like shaped and vivid purplish-red pink marginal floral bracts around inflorescence;
(3) many flowers attach to lower branches;.
(4) elegant rose-like fragrance of flowers;
(5) strong disease resistance, especially to powdery mildew.

'SFCG1702' has plant characteristics of upright plant growth habit, spectacular extremely large and vivid purplish-red pink colored floral bracts, and elegant rose-like fragrance, so that it is suitable as a street tree and a garden tree.

Since 'SFCG1702' has upright plant growth habit and is less likely to spread branches transversely, it can be densely planted even in a relatively narrow street or house garden. In addition, the branches of 'SFCG1702' are less likely to be broken off from a tree due to accumulated snow. Furthermore, cultivation management of 'SFCG1702' is relatively easy, because it does not require frequent pruning, and has strong disease resistance especially to powdery mildew.

'SFCG1702' has four extremely large, heart-like shaped and vivid purplish-red pink marginal floral bracts around each inflorescence, and many flowers attach to lower branches, so that it has excellent ornamental value.

'SFCG1702' clearly differs from its seed parent cultivar 'White Love', due to its vivid purplish-red pink colored floral bracts and elegant rose-like fragrance.

In addition, 'SFCG1702' clearly differs from the representative cultivar of red flowering dogwoods 'Cherokee Chief', which has semi-upright plant growth habit and small red flowers, in the point that 'SFCG1702' has upright plant growth habit, and extremely large, vivid purplish-red pink marginal floral bracts and elegant rose-like fragrance.

It should be noted that the plant age of all the plants of 'SFCG1702', which were observed for botanical description, was 3 years.

BRIEF DESCRIPTION OF THE DRAWINGS

This new cultivar of dogwood is illustrated by the accompanying digital color photographs, depicting defining characteristics of the plant by the best possible color photography. Colors of foliage, flowers and other plant parts may vary from year to year depending on, among other factors, horticultural practices, light conditions, air temperature, soil fertility, etc.

BOTANICAL DESCRIPTION OF THE INVENTION

Figure 1:
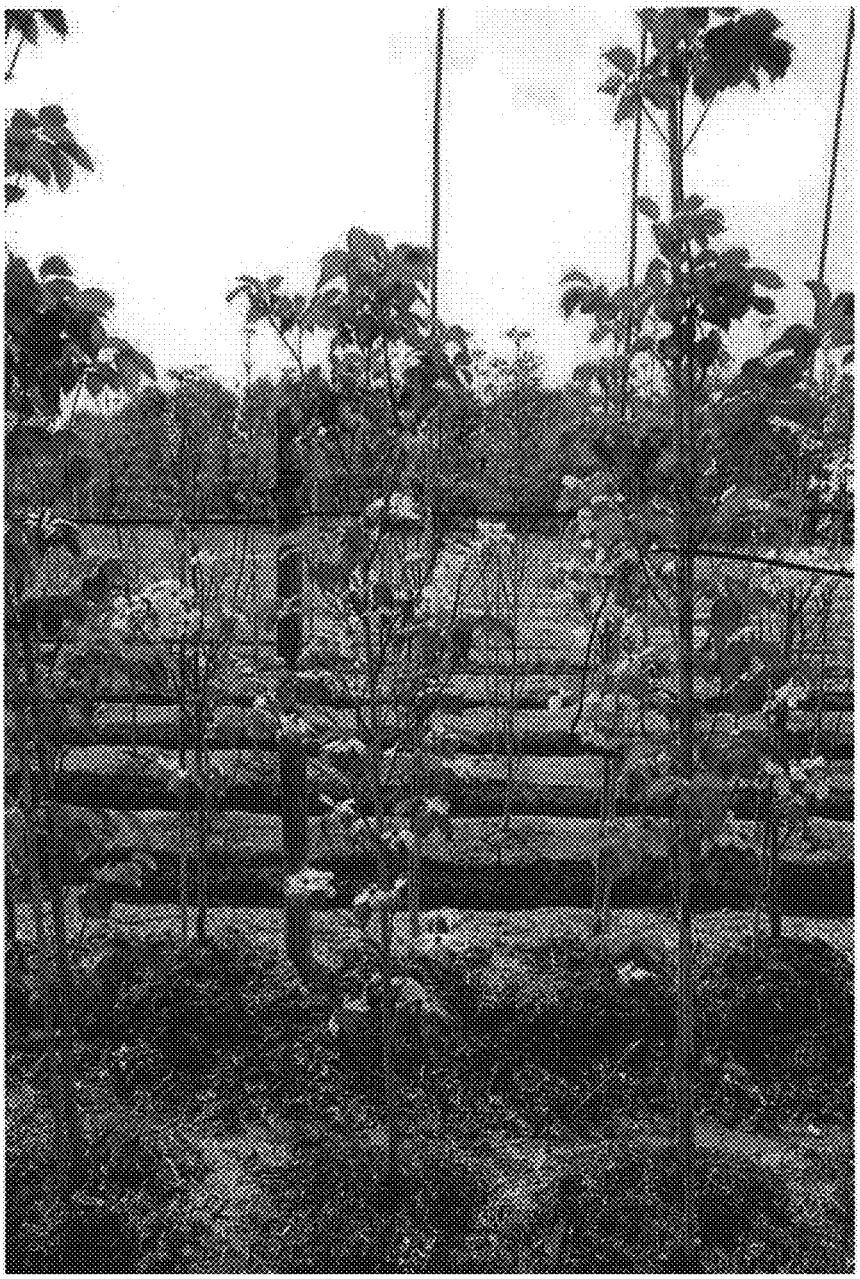
FIG. 1 illustrates an entire tree of 'SFCG1702' in bloom (photographed date: Apr. 23, 2018; photographed location: Inazawa-City, Aichi-prefecture, Japan; and the age of photographed 'SFCG1702': 3 years).
Figure 2:
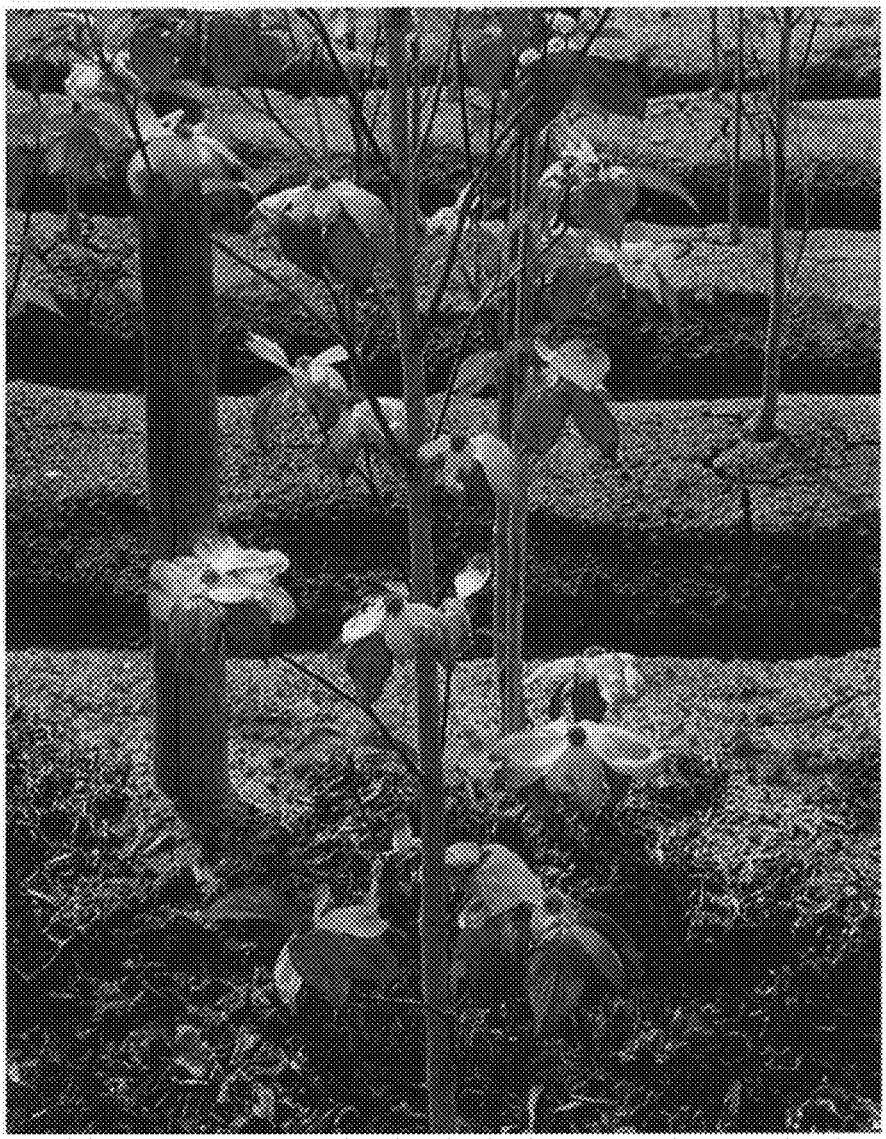
FIG. 2 illustrates multiple sets of an inflorescence and four floral bracts of 'SFCG1702' on a tree (photographed date: Apr. 23, 2018; photographed location: Inazawa-City, Aichi-prefecture, Japan; and the age of photographed 'SFCG1702': 3 years).
Figure 3:
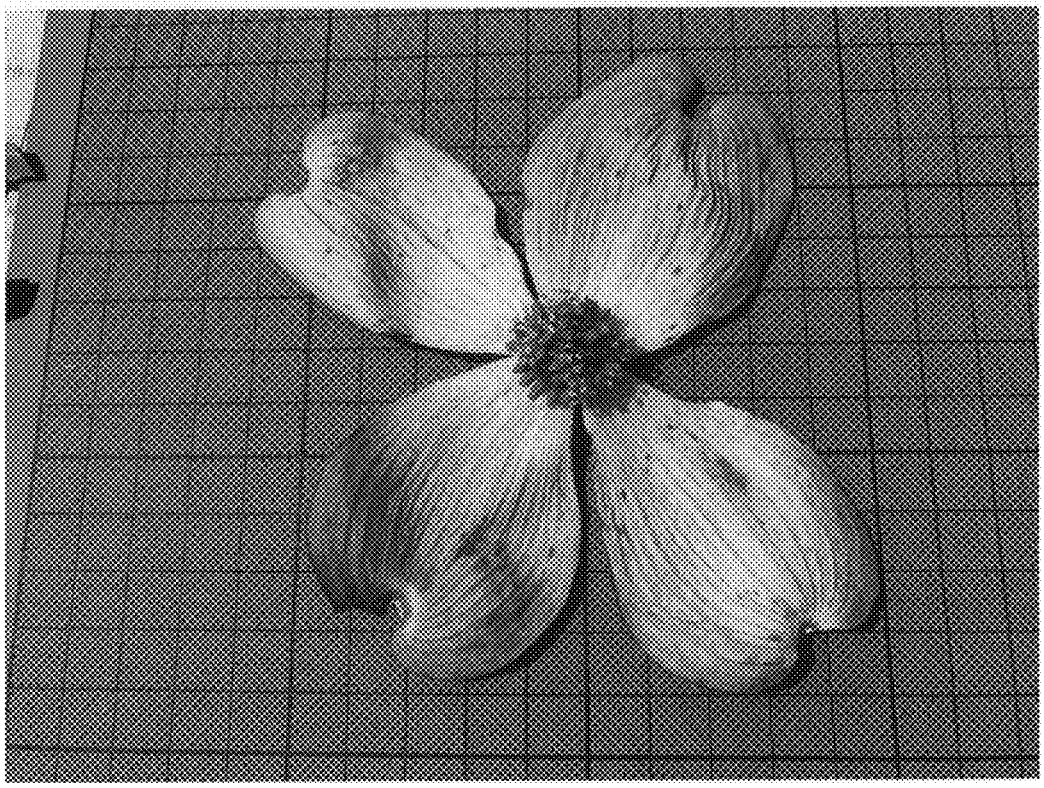
FIG. 3 illustrates the size of one set of an inflorescence and four floral bracts of 'SFCG1702' on 1 cm grid cutting mat (photographed date: Apr. 25, 2017; photographed location: Inazawa-City, Aichi-prefecture, Japan; and the age of photographed 'SFCG1702': 3 years).
Figure 4:
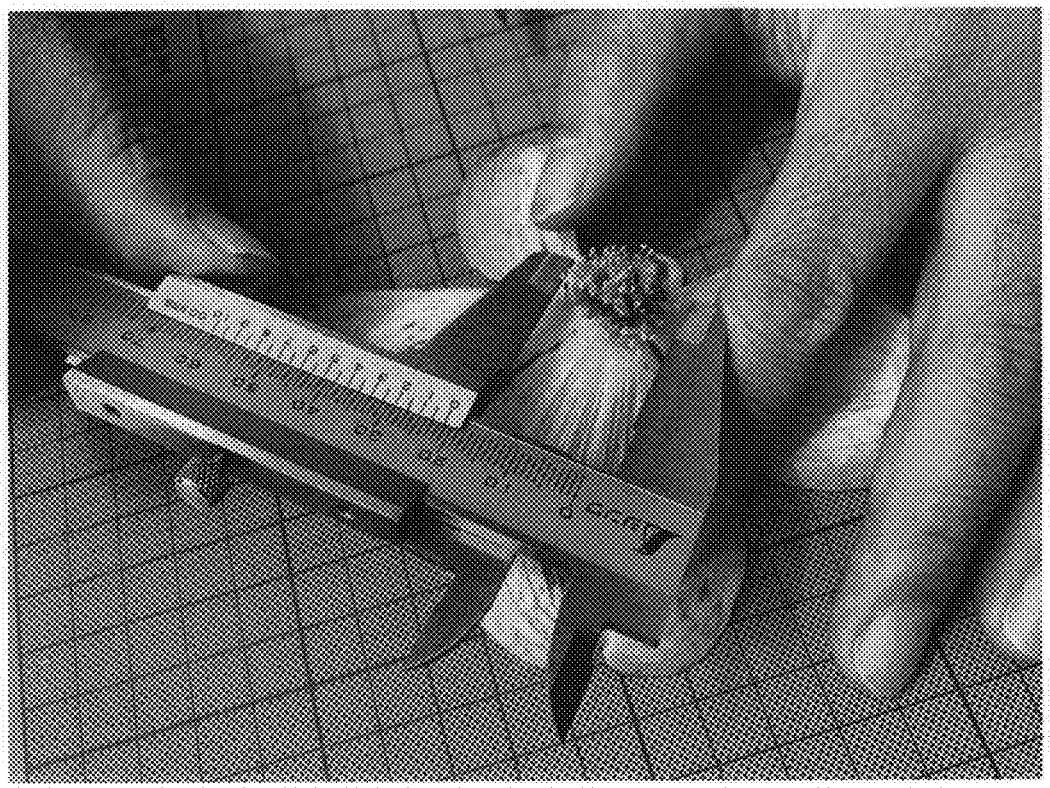
FIG. 4 illustrates the size of an inflorescence of 'SFCG1702' shown on a vernier caliper (photographed date: Apr. 26, 2016; photographed location: Inazawa-City, Aichi-prefecture, Japan; and the age of photographed 'SFCG1702': 3 years).
Figure 5:
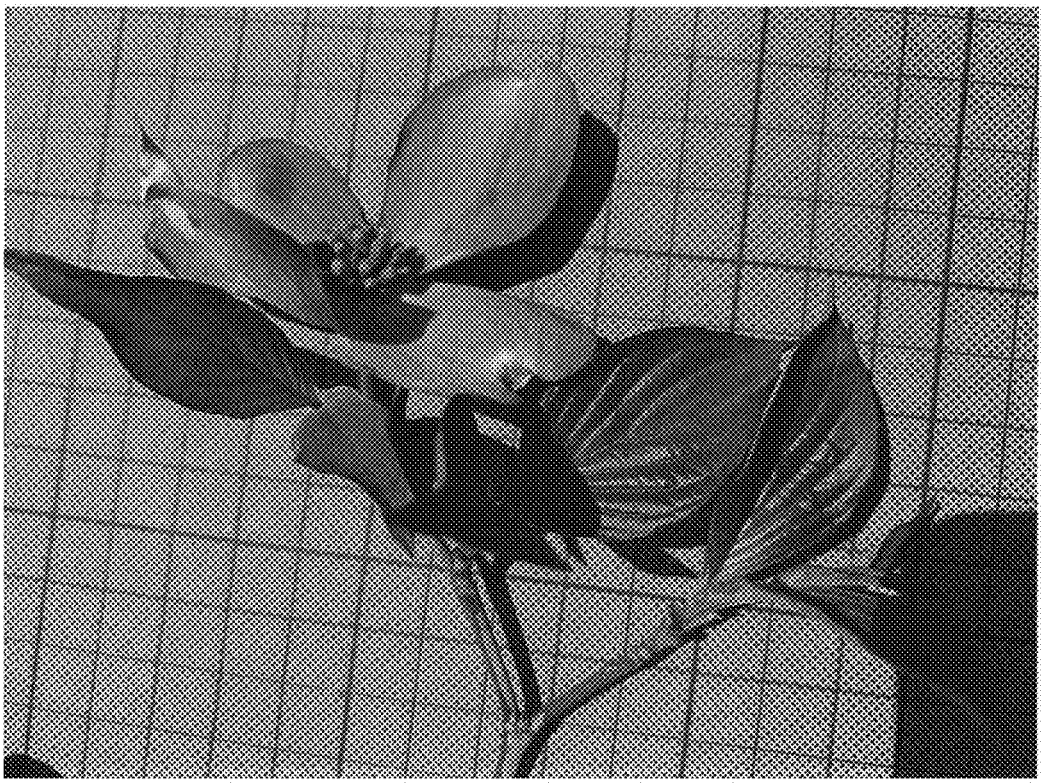
FIG. 5 illustrates the size of one set of an inflorescence and four floral bracts of the similar cultivar 'Cherokee Chief' on 1 cm grid cutting mat (photographed date: Jul. 25, 2017; photographed location: Inazawa-City, Aichi-prefecture, Japan; and the age of photographed 'Cherokee Chief': 3 years).
Figure 6:
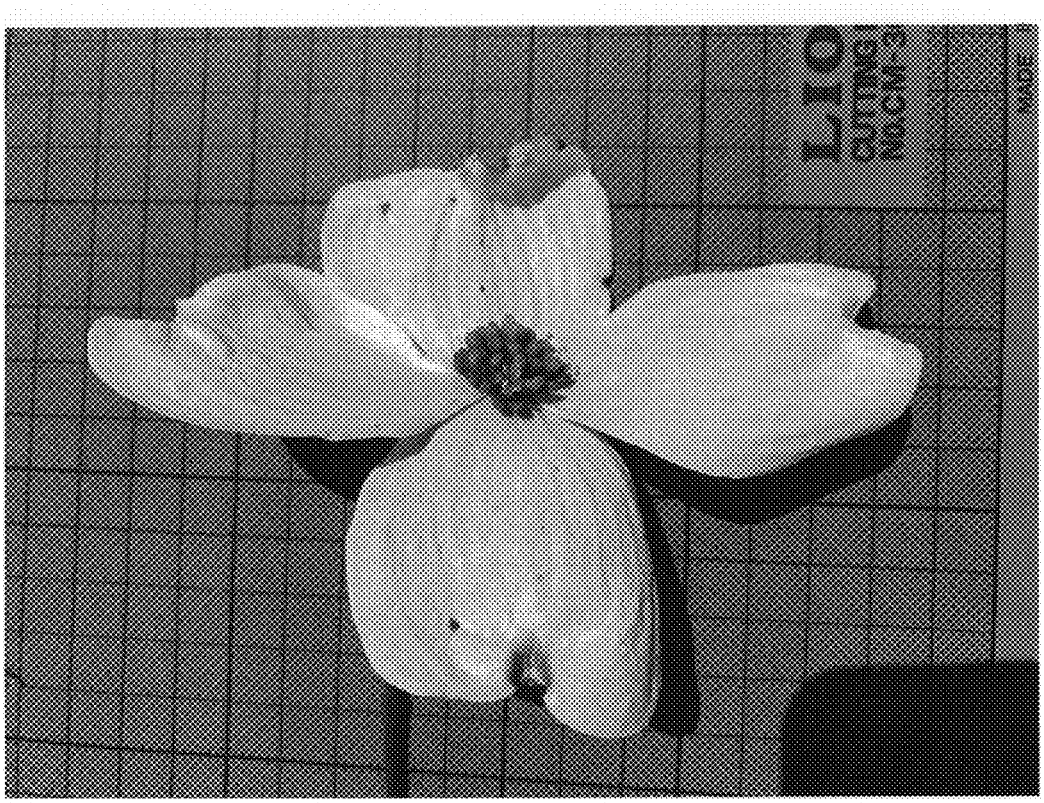
FIG. 6 illustrates the size of one set of an inflorescence and four floral bracts of the similar cultivar (seed parent) 'White Love' on 1 cm grid cutting mat (photographed date: Apr. 25, 2017; photographed location: Inazawa-City, Aichi-prefecture, Japan; and the age of photographed 'White Love': 3 years).
Figure 7:
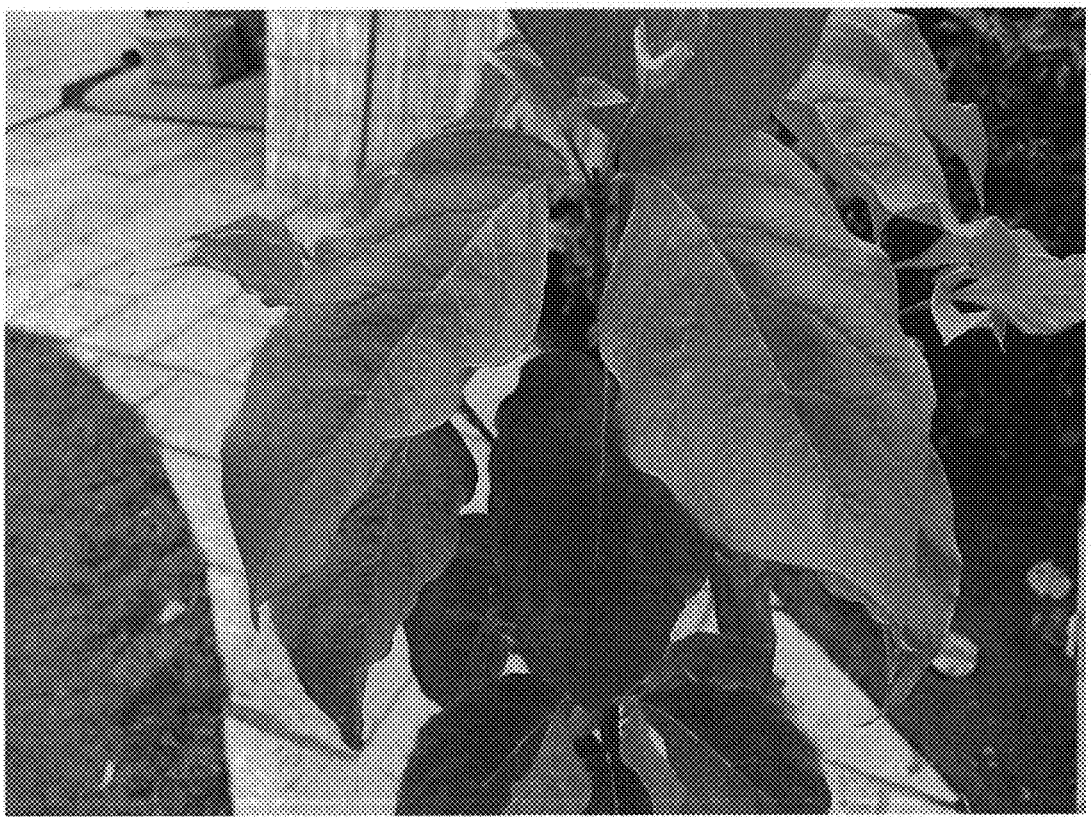
FIG. 7 illustrates elliptic leaves of 'SFCG1702' in growing season (photographed date: Sep. 23, 2016; photographed location: Inazawa-City, Aichi-prefecture, Japan; and the age of photographed 'SFCG1702': 3 years).
Figure 8:
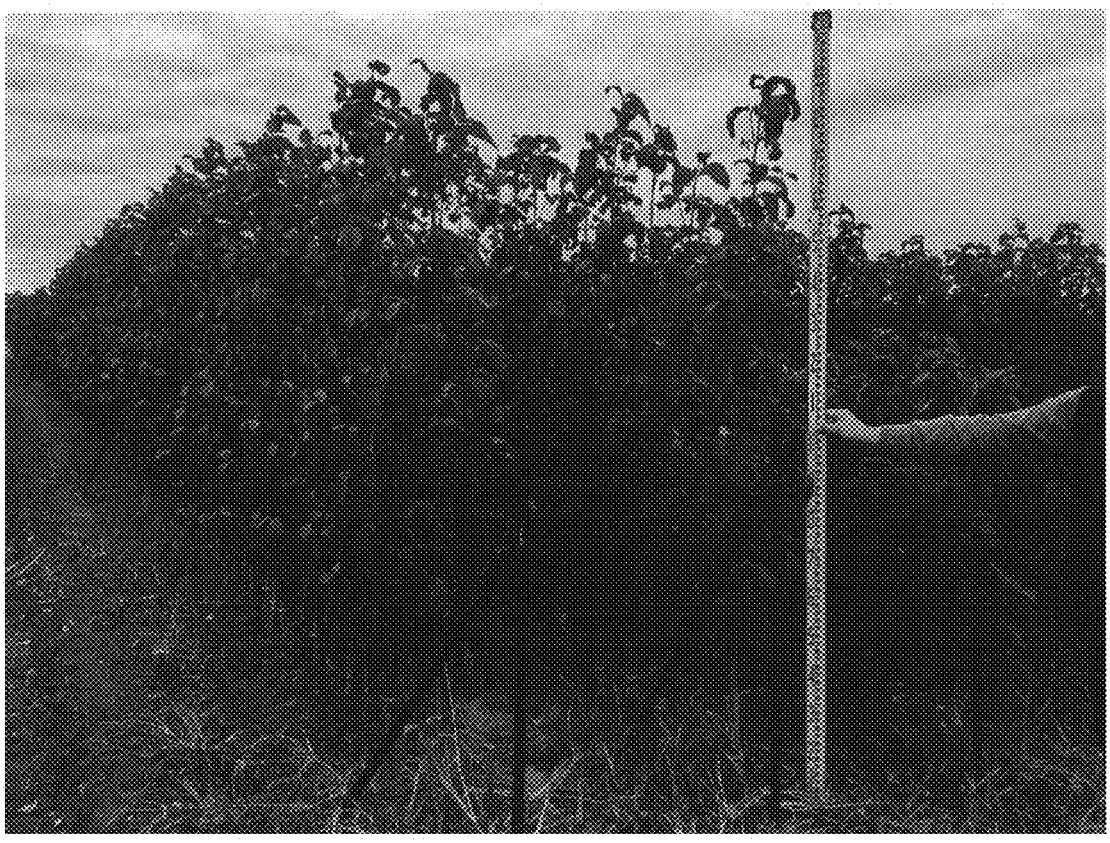
FIG. 8 illustrates the height of a tree of 'SFCG1702' in fall autumn leaves (photographed date: Nov. 13, 2018; photographed location: Inazawa-City, Aichi-prefecture, Japan; and the age of photographed 'SFCG1702': 3 years).
Figure 9:
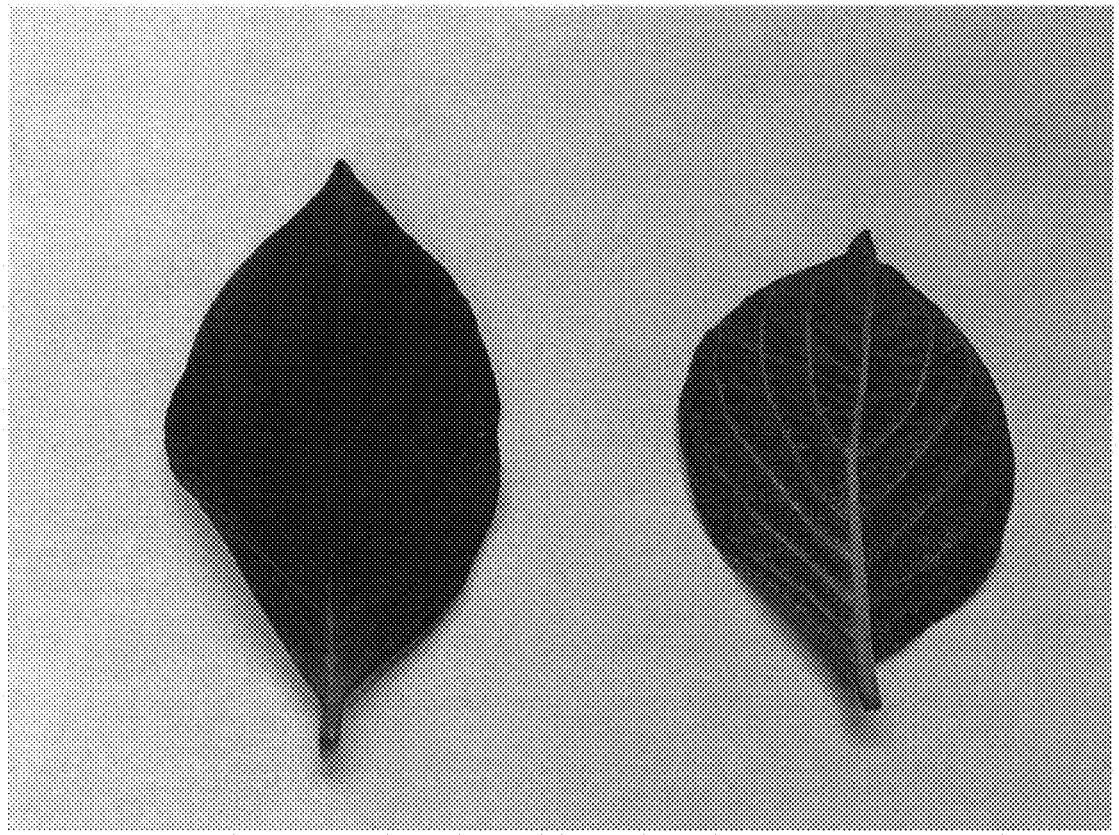
FIG. 9 illustrates an upper surface and a lower surface of two leaves of 'SFCG1702', respectively (photographed date: Apr. 19, 2016; photographed location: Inazawa-City, Aichi-prefecture, Japan; and the age of photographed 'SFCG1702': 3 years).
Figure 10:
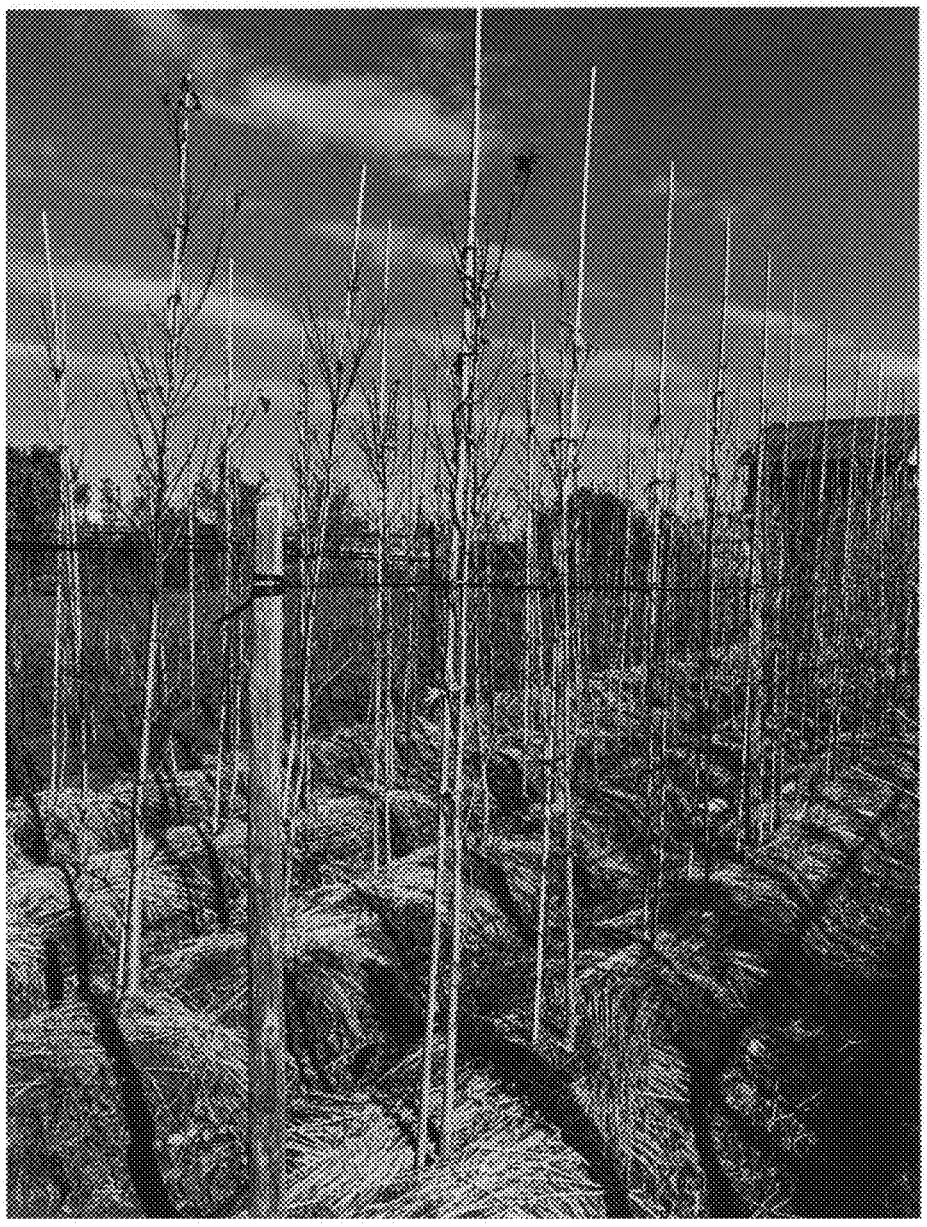
FIG. 10 illustrates an entire tree of 'SFCG1702' without foliage (photographed date: Mar. 7, 2019; photographed location: Inazawa-City, Aichi-prefecture, Japan; and the age of photographed 'SFCG1702': 3 years).
Figure 11:
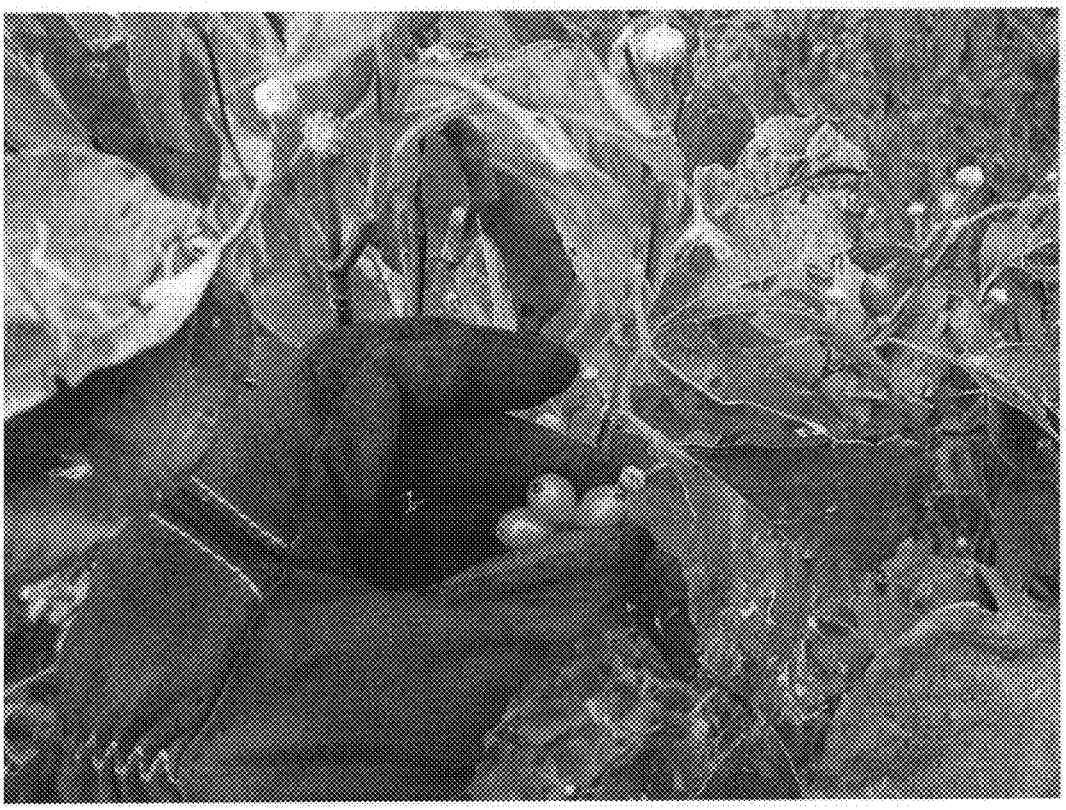
FIG. 11 illustrates vivid reddish orange colored fruits of 'SFCG1702' (photographed date: Oct. 24, 2016; photographed location: Minuma-Ward, Saitama-City, Saitama-prefecture, Japan; and the age of photographed 'SFCG1702': 3 years).

1. Plant:
   *Form*.—Tree.
   *Growth habit*.—Upright.
   *Plant height*.—High (0.6 m at 1-year).
   *Plant spread*.—Narrow (7 cm at 1-year).
   *Cold hardiness*.—Almost the same as that of 'Cherokee Chief' (to −10° C.).
   *Heat tolerance*.—Almost the same as that of 'Cherokee Chief' (to +40° C.).
   *Resistance to disease*.—Stronger than that of 'Cherokee Chief', especially to powdery mildew.
   *Resistance to insects*.—Almost the same as that of 'Cherokee Chief'.
2. Branches:
   *Diameter of branches*.—Narrow (average diameter 2.2 cm; range 1.9-2.5 cm, n=10).
   *Color of shoots* (*April*).—Strong Yellow Green (RHS Code: 145A).
   *Color of branches*.—Dark Red (RHS Code: 183A).
   *Surface pattern of branches*.—None.
   *Ramification*.—Almost the same as that of 'Cherokee Chief'.
   *Internode length*.—Average length 9.7 cm (range 7.3-14.5 cm, n=10).

*The angle of the intermediate portion of a branch to the trunk in the intermediate portion of tree.*—29.2° on average (range 25°-33° , n=10).

3. Leaves:
   - *Leaf shape.*—Elliptic.
   - *Leaf tip shape.*—Apiculate.
   - *Leaf base shape.*—Obtuse.
   - *Leaf margin shape.*—Entire.
   - *Curvature of leaf.*—Turn outward.
   - *Undulation of leaf margin.*—None.
   - *Leaf blade length.*—Average length 10.6 cm (range 9.9-12.6 cm, n=10).
   - *Leaf blade width.*—Average width 5.4 cm (range 4.7-6.0 cm, n=10).
   - *Thickness of leaf blade.*—Almost the same as that of 'Cherokee Chief' and general dogwoods.
   - *Color of new bud.*—Dark Red (RHS Code: 183B).
   - *Color of new leaf.*—Grayish brown (RHS Code: 166A).
   - *Color of upper surface of mature leaf.*—Moderate Olive Green (RHS Code: 147A).
   - *Color of lower surface of mature leaf.*—Pale Green (RHS Code: 190B).
   - *Changeability of leaf color.*—No change between new leaf and mature leaf prior to change to autumn color.
   - *Color of autumn leaf (mid-October).*—Dark Red (RHS Code: 187B).
   - *Mottle on leaf.*—None.
   - *Glossiness of leaf blade.*—Lustrous.
   - *Hairs on upper surface of leaf.*—Almost the same as that of 'Cherokee Chief'.
   - *Hairs on lower surface of leaf.*—Fewer than that of 'Cherokee Chief'.
   - *Leaf veins.*—Easily visible.
   - *Diameter of petiole.*—Average diameter 1.5 mm (range 1.0-2.0 mm, n=10).
   - *Length of petiole.*—Average length 9.7 mm (range 6.0-13.5 mm, n=10).
   - *Color of petiole.*—Brilliant Yellow Green (RHS Code: 150A).

4. Flowers:
   - *Inflorescence.*—
   - *Type of inflorescence.*—Flower head. dense, rounded mound.
   - *Direction of inflorescence.*—Upward facing.
   - *Size of inflorescence (flower head).*—Average diameter 20.2 mm (range 17.5-21.0 mm, n=10).
   - *Size of inflorescence including floral bracts.*—Average diameter 11.3 cm (range 10.9-12.8 mm, n=10).
   - *Floret (true flower).*—
   - *Size of floret.*—Average diameter 3.5 mm (range 3.0-4.0 mm, n=10).
   - *Color of floret.*—Strong Greenish Yellow (RHS Code: 151B).
   - *Shape of floret.*—Rounded.
   - *Floral bracts.*—
   - *Flowering habit.*—Single-flowered.
   - *Overlapping of floral bracts.*—Overlapping.
   - *Opening habit of floral bracts.*—Horizontal.
   - *Warping habit of floral bracts.*—Horizontal.
   - *Degree of warping of floral bracts.*—Extremely weak.
   - *Curvature of floral bracts.*—Horizontal.
   - *Twist of floral bracts.*—None.
   - *Shape of entire floral bract.*—Obovate.
   - *Shape of tip of floral bract.*—Concave shape.
   - *Length of floral bract.*—Average length 54.1 mm (range 51-61 mm, n=10).
   - *Width of floral bract.*—Average width 46.8 mm (range 42.1-56.0 mm, n=10).
   - *Number of floral bracts.*—Four (two opposing pairs).
   - *Color of floral bracts (base color).*—Greenish white (RHS Code: 155C).
   - *Pattern of floral bracts.*—Vein pattern.
   - *Color of pattern of floral bracts.*—Vivid purplish Red (RHS Code: N57B).
   - *Diameter of peduncle.*—Average diameter 2.1 mm (range 1.6-1.9 mm, n=10).
   - *Length of peduncle.*—Average length 28.3 mm (range 23.2-31.5 mm, n=10).
   - *Color of peduncle.*—Brilliant Yellow Green (RHS Code: 149A).
   - *Fragrance of flower.*—Elegant rose-like fragrance.

5. Reproductive organs:
   - *Color of pistil.*—Strong Yellow Green (RHS Code: 144A).
   - *Color of stamen.*—Pale Yellow Green (RHS Code: 155A).

6. Fruit
   - *Shape of fruit.*—Elliptic.
   - *Length of fruit.*—Almost the same as that of 'Cherokee Chief' (average 1.3 mm; range 1.1-1.6 mm, n=10).
   - *Width of fruit.*—Almost the same as that of 'Cherokee Chief' (average 0.9 mm; range 0.7-1.1 mm, n=10).
   - *Color of fruit.*—Vivid Reddish Orange (RHS Code: 44B).

7. Others:
   - *Fertile property.*—High (Almost the same as that of 'Cherokee Chief').
   - *Blooming.*—One-season blooming. The first ornamental display of the large floral bracts are observed around April 20 in Aichi-prefecture, Japan, and the floral display of the large floral bracts typically lasts about ten days, depending on weather conditions.
   - *Defoliation.*—Deciduous.
   - *Time of fruit maturity.*—Late October in Aichi-prefecture, Japan.

What is claimed is:

1. A new and distinct cultivar of *Cornus florida* L. plant (dogwood tree) named 'SFCG1702', substantially as herein illustrated and described, characterized particularly as to novelty by exhibiting upright plant growth habit, and extremely large, vivid purplish-red pink marginal floral bracts.

* * * * *